(12) United States Patent
Stahmann et al.

(10) Patent No.: US 10,849,545 B2
(45) Date of Patent: Dec. 1, 2020

(54) ACUTE KIDNEY INJURY DETECTION SYSTEM AND METHODS

(71) Applicant: Cardiac Pacemakers, Inc., St. Paul, MN (US)

(72) Inventors: Jeffrey E. Stahmann, Ramsey, MN (US); Michael John Kane, St. Paul, MN (US); Pramodsingh Hirasingh Thakur, Woodbury, MN (US); Ramesh Wariar, Blaine, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 155 days.

(21) Appl. No.: 15/610,769

(22) Filed: Jun. 1, 2017

(65) Prior Publication Data
US 2017/0347936 A1 Dec. 7, 2017

Related U.S. Application Data

(60) Provisional application No. 62/344,605, filed on Jun. 2, 2016.

(51) Int. Cl.
*A61B 5/20* (2006.01)
*A61B 5/145* (2006.01)
(Continued)

(52) U.S. Cl.
CPC .......... *A61B 5/201* (2013.01); *A61B 5/0031* (2013.01); *A61B 5/0205* (2013.01); *A61B 5/026* (2013.01);
(Continued)

(58) Field of Classification Search
None
See application file for complete search history.

(56) References Cited

U.S. PATENT DOCUMENTS 4,291,692 A * 9/1981 Bowman ............ A61B 5/14507 604/151
4,658,834 A * 4/1987 Blankenship .......... A61B 5/208 600/584

(Continued)

FOREIGN PATENT DOCUMENTS

EP 2769672 8/2014
WO 2009138976 11/2009
(Continued)

OTHER PUBLICATIONS

International Search Report and Written Opinion for PCT Application No. PCT/US2017/035354 dated Aug. 25, 2017 (13 pages).
(Continued)

*Primary Examiner* — Carl H Layno
*Assistant Examiner* — Manolis Pahakis
(74) *Attorney, Agent, or Firm* — Pauly, DeVries Smith & Deffner LLC

(57) ABSTRACT

Embodiments herein include systems and methods for detecting, predicting and/or assessing acute kidney injury. In an embodiment, a monitoring system to detect acute kidney injury is included. The monitoring system can include a sensor circuit configured to collect renal data including at least one of systemic renal data, direct renal data, urinary tract data, and renal-relevant extracorporeal data. The monitoring system can also include a memory circuit to store collected renal data, an evaluation circuit to assess renal status, and a telemetry circuit. The evaluation circuit can determine whether acute kidney injury has occurred or is likely to occur by comparing the renal data to at least one of threshold values, personal historical values, patient population values and patterns indicative of acute kidney injury. The evaluation circuit can initiate a warning notification if
(Continued)

acute kidney injury has occurred or is likely to occur. Other embodiments are also included herein.

15 Claims, 7 Drawing Sheets

(51) Int. Cl.

| | | |
|---|---|---|
| A61B 5/00 | (2006.01) | |
| A61B 5/1459 | (2006.01) | |
| A61B 5/1486 | (2006.01) | |
| G01N 27/327 | (2006.01) | |
| A61B 5/1473 | (2006.01) | |
| A61B 5/0205 | (2006.01) | |
| A61B 5/026 | (2006.01) | |
| A61B 5/07 | (2006.01) | |
| G01N 33/483 | (2006.01) | |
| G08B 21/04 | (2006.01) | |
| A61B 5/02 | (2006.01) | |
| A61B 5/08 | (2006.01) | |
| A61B 5/0245 | (2006.01) | |
| G16H 10/60 | (2018.01) | |
| G16H 50/30 | (2018.01) | |
| A61B 5/021 | (2006.01) | |
| G06F 19/00 | (2018.01) | |

(52) U.S. Cl.
CPC ............ *A61B 5/076* (2013.01); *A61B 5/1459* (2013.01); *A61B 5/1473* (2013.01); *A61B 5/14503* (2013.01); *A61B 5/14507* (2013.01); *A61B 5/14532* (2013.01); *A61B 5/14539* (2013.01); *A61B 5/14546* (2013.01); *A61B 5/14865* (2013.01); *A61B 5/205* (2013.01); *A61B 5/208* (2013.01); *A61B 5/4848* (2013.01); *A61B 5/4875* (2013.01); *A61B 5/6861* (2013.01); *A61B 5/7264* (2013.01); *A61B 5/7275* (2013.01); *A61B 5/7282* (2013.01); *A61B 5/746* (2013.01); *G01N 27/3273* (2013.01); *G01N 33/483* (2013.01); *G08B 21/0453* (2013.01); *A61B 5/021* (2013.01); *A61B 5/02028* (2013.01); *A61B 5/0245* (2013.01); *A61B 5/0816* (2013.01); *A61B 5/204* (2013.01); *A61B 2505/07* (2013.01); *A61B 2560/0475* (2013.01); *G01N 2800/347* (2013.01); *G06F 19/324* (2013.01); *G06F 19/3418* (2013.01); *G16H 10/60* (2018.01); *G16H 50/30* (2018.01)

(56) References Cited

U.S. PATENT DOCUMENTS

| | | | |
|---|---|---|---|
| 6,237,398 B1 | 5/2001 | Porat et al. | |
| 6,454,707 B1* | 9/2002 | Casscells, III | A61B 5/01 600/300 |
| 6,589,229 B1 | 7/2003 | Connelly et al. | |
| 6,725,447 B1* | 4/2004 | Gilman | G06F 19/325 717/105 |
| 6,978,182 B2 | 12/2005 | Mazar et al. | |
| 7,400,920 B1* | 7/2008 | Gill | A61B 5/201 600/509 |
| 7,529,580 B2* | 5/2009 | Gill | A61B 5/0452 600/509 |
| 7,809,441 B2* | 10/2010 | Kane | A61B 5/14546 600/322 |
| 8,126,554 B2 | 2/2012 | Kane et al. | |
| 8,457,761 B2 | 6/2013 | Wariar et al. | |
| 8,463,346 B2* | 6/2013 | Kuhn | A61B 5/1459 600/322 |
| 9,554,725 B2* | 1/2017 | Katra | A61M 1/14 |
| 9,616,107 B2* | 4/2017 | VanAntwerp | A61K 9/0019 |
| 2003/0083585 A1* | 5/2003 | Oort | A61B 5/0456 600/510 |
| 2006/0100743 A1* | 5/2006 | Townsend | A61B 5/14507 700/266 |
| 2007/0038138 A1* | 2/2007 | Gill | A61B 5/0452 600/513 |
| 2007/0208382 A1* | 9/2007 | Yun | A61N 1/36007 607/2 |
| 2009/0105799 A1* | 4/2009 | Hekmat | A61B 5/201 623/1.11 |
| 2009/0285761 A1* | 11/2009 | Wang | A61B 5/0071 424/9.6 |
| 2010/0016746 A1* | 1/2010 | Hampton | A61B 5/0452 600/523 |
| 2010/0121220 A1 | 5/2010 | Nishtala et al. | |
| 2010/0228148 A1* | 9/2010 | Kim | A61B 5/412 600/573 |
| 2010/0286559 A1* | 11/2010 | Paz | A61B 5/14507 600/581 |
| 2012/0065501 A1* | 3/2012 | Dae | A61N 7/00 600/431 |
| 2012/0095304 A1* | 4/2012 | Biondi | G16H 50/20 600/301 |
| 2012/0277546 A1* | 11/2012 | Soykan | A61B 5/0205 600/301 |
| 2013/0144176 A1* | 6/2013 | Lee | A61B 5/0002 600/485 |
| 2013/0274705 A1* | 10/2013 | Burnes | A61M 5/1723 604/505 |
| 2013/0310706 A1* | 11/2013 | Stone | A61B 8/56 600/561 |
| 2014/0031787 A1* | 1/2014 | Burnes | A61B 5/4836 604/505 |
| 2014/0088992 A1* | 3/2014 | Fuchs | G16H 50/20 705/2 |
| 2014/0107432 A1* | 4/2014 | Bastia | A61B 5/202 600/301 |
| 2014/0184422 A1 | 7/2014 | Mensinger et al. | |
| 2014/0235503 A1 | 8/2014 | Kim et al. | |
| 2014/0276100 A1* | 9/2014 | Satterfield | A61B 5/082 600/476 |
| 2015/0157275 A1* | 6/2015 | Swamy | A61B 5/7275 600/301 |
| 2016/0078195 A1* | 3/2016 | Sarkar | G16H 10/20 705/3 |
| 2016/0147958 A1* | 5/2016 | Vairavan | G06F 19/325 705/3 |
| 2016/0003810 A1 | 7/2016 | Yamagata et al. | |
| 2016/0310711 A1* | 10/2016 | Luxon | A61M 27/00 |
| 2017/0035342 A1* | 2/2017 | Elia | A61B 5/7475 |
| 2017/0136209 A1* | 5/2017 | Burnett | A61M 1/0031 |
| 2017/0281095 A1* | 10/2017 | An | A61B 5/02 |
| 2017/0281096 A1* | 10/2017 | Zhang | A61B 5/11 |
| 2017/0347936 A1* | 12/2017 | Stahmann | A61B 5/0205 |
| 2018/0110455 A1* | 4/2018 | Chang | A61B 5/201 |
| 2018/0128838 A1* | 5/2018 | Bergmann | G01N 33/6893 |
| 2018/0177458 A1* | 6/2018 | Burnett | A61B 5/01 |
| 2019/0069830 A1* | 3/2019 | Holt | A61B 5/7207 |

FOREIGN PATENT DOCUMENTS

| | | | |
|---|---|---|---|
| WO | 2013121290 | 8/2013 | |
| WO | 2013154783 | 10/2013 | |
| WO | WO-2014043650 A2 * | 3/2014 | ......... A61B 5/14507 |
| WO | 2015192054 | 12/2015 | |
| WO | 2016019250 | 2/2016 | |
| WO | 2017210377 | 12/2017 | |

OTHER PUBLICATIONS

"Acute Kidney Injury: the most deadly disease you've never heard of," Astute Medical Fact Sheet URL <http://www.astutemedical.com/up-content/uploads/2015/07/AKI_Fact_Sheet_PN-0104_RevD.pdf> downloaded Jun. 19, 2017 (4 pages).

(56) References Cited

OTHER PUBLICATIONS

"Adding Insult to Injury: a review of the care of patients who died in hospital with a primary diagnosis of acute kidney injury," A report by the National Confidential Enquiry into Patient Outcome and Death, 2009 (100 pages).

"American Society of Nephrology Renal Research Report," J. Am. Soc. Nephrol. 2005; 16: 1886-1903 (18 pages).

Brown, Jeremiah R. et al., "Impact of Perioperative Acute Kidney Injury as a Severity Index for Thirty-Day Readmission After Cardiac Surgery," Ann. Thorac. Surg. 2014; 97(1): 111-117 (7 pages).

"Ckd: Chapter Six—Acute Kidney Injury," United States Renal Data System Annual Data Report; 2013 (12 pages).

Conger, J. "A controlled evaluation of prophylactic dialysis in post-traumatic acute renal failure," J. Trauma Inj. Inf. & Crit. Cr. 1975; 15:1056-1063 (10 pages).

Dasta, Joseph F. et al., "Costs and Outcomes of Acute Kidney Injury (AKI) Following Cardiac Surgery," Nephrol. Dial. Transplant (2008) 23: 1970-1974 (5 pages).

Hobson, Charles et al., "Cost and Mortality Associated with Postoperative Acute Kidney Injury," Ann. Surg. Jun. 2015; 261(6): 1207-1214 (18 pages).

Kleinknecht, Dieter et al., "Uremic and non-uremic complications in acute renal failure: Evaluation of early and requent dialysis on prognosis," Kidney International, vol. 1 (1972), p. 190-196 (7 pages).

Lameire, Norbert et al., "Acute Renal Failure," The Lancet 365:417-430, 2005 (14 pages).

Lewington, Andrew et al., "Raising Awareness of Acute Kidney Injury: A Global Perspective of a Silent Killer," Kidney Int. Sep. 2013; 84(3): 457-467 (25 pages).

Liano, Fernando et al., "Epidemiology of acute renal failure: A prospective, multicenter, community-based study," Kidney International 1996; 50: 811-818 (8 pages).

Susantitaphong, Paweena "World Incidence of AKI: A Meta-Analysis," Clin. J. Am. Soc. Nephrol. 8: 1482-1493, 2013 (12 pages).

Uchino, Shigehiko et al., "Acute Renal Failure in Critically Ill Patients: A multinational, Multicenter Study," JAMA 2005; 294:813-818 (6 pages).

International Preliminary Report on Patentability for PCT Application No. PCT/US2017/035354 dated Dec. 13, 2018 (9 pages).

\* cited by examiner

ACUTE KIDNEY INJURY DETECTION SYSTEM AND METHODS

This application claims the benefit of U.S. Provisional Application No. 62/344,605, filed Jun. 2, 2016, the contents of which are herein incorporated by reference.

FIELD

Embodiments herein relate to systems and methods for detecting, predicting and/or assessing acute kidney injury.

BACKGROUND

Acute kidney injury (AKI) is the abrupt loss of kidney function, resulting in the retention of urea and other nitrogenous waste products and in the dysregulation of extracellular volume and electrolytes. AKI can be fatal and requires immediate and intensive treatment. If treated appropriately and in time, AKI is often reversible.

Causes of AKI are frequently classified as prerenal, intrinsic, or post-renal. Prerenal causes of AKI are those that decrease effective blood flow to the kidney. Sources of damage to the kidney itself are dubbed intrinsic causes. Post-renal causes of AKI are those resulting in urinary tract obstruction.

SUMMARY

Embodiments herein include systems and methods for detecting, predicting and/or assessing acute kidney injury. In some examples, systems are included such as a monitoring system to detect acute kidney injury. The monitoring system can include one or more sensor circuits configured to collect renal data including at least one of systemic renal data, direct renal data, urinary tract data, and renal-relevant extracorporeal data. The monitoring system can also include a memory circuit to store collected renal data. The monitoring system can also include an evaluation circuit configured to receive the renal data from at least one of the sensor circuit and the memory circuit and assess renal status. The monitoring system can also include a telemetry circuit in electronic communication with at least one of the sensor circuit and the evaluation circuit. The evaluation circuit can determine whether acute kidney injury has occurred or is likely to occur by comparing the renal data to at least one of threshold values, personal historical values, patient population values and patterns indicative of acute kidney injury. The evaluation circuit can be configured to initiate a warning notification if acute kidney injury has occurred or is likely to occur.

In addition to other aspects, or in the alternative, another aspect can include wherein the sensor circuit collects at least two of systemic renal data, direct renal data, urinary tract data and renal-relevant extracorporeal data.

In addition to other aspects, or in the alternative, another aspect can include wherein the sensor circuit collects at least three of systemic renal data, direct renal data, urinary tract data and renal-relevant extracorporeal data.

In addition to other aspects, or in the alternative, another aspect can include wherein the sensor circuit collects systemic renal data, direct renal data, urinary tract data and renal-relevant extracorporeal data.

In addition to other aspects, or in the alternative, another aspect can include, wherein at least one of the sensor circuit, memory circuit, evaluation circuit and telemetry circuit are at least partially housed in an implanted device.

In addition to other aspects, or in the alternative, another aspect can include wherein at least one of the sensor circuit, memory circuit, evaluation circuit and telemetry circuit are housed in a wearable device.

In addition to other aspects, or in the alternative, another aspect can include wherein the telemetry circuit conveys renal data to the evaluation circuit and the evaluation circuit is located remotely from the sensor circuit.

In addition to other aspects, or in the alternative, another aspect can include wherein the telemetry circuit conveys the renal data to a remotely located server containing the evaluation circuit.

In addition to other aspects, or in the alternative, another aspect can include the remotely located server configured to execute a pattern recognition algorithm to classify the patient as either currently suffering from acute renal injury, imminently likely to suffer acute renal injury, or not suffering from acute renal injury and not imminently likely to suffer acute renal injury.

In addition to other aspects, or in the alternative, another aspect can include wherein the evaluation circuit calculates a risk index score indicative of the patient's risk of suffering an acute kidney injury.

In addition to other aspects, or in the alternative, another aspect can include wherein the evaluation circuit places the patient into a category indicative of the patient's risk of suffering an acute kidney injury.

In addition to other aspects, or in the alternative, another aspect can include wherein the evaluation circuit estimates at least one of glomerular filtration rate and fractional excretion of filtered sodium.

In addition to other aspects, or in the alternative, another aspect can include the systemic renal data including at least one of hydration status, volumetric status, and hemodynamic status.

In addition to other aspects, or in the alternative, another aspect can include the direct renal data including at least one of renal blood pressure and renal blood flow. In addition to other aspects, or in the alternative, another aspect can include the urinary tract data including at least one of urine pressure, urine flow, and a urine biophysical characteristic.

In addition to other aspects, or in the alternative, another aspect can include the urine biophysical characteristic comprising a urine biomarker.

In addition to other aspects, or in the alternative, another aspect can include the urine biomarker selected from the group consisting of creatinine, sodium, albumin, protein, bacteria, myoglobin, nitrates, pH, glucose and urinary casts.

In addition to other aspects, or in the alternative, another aspect can include wherein the evaluation circuit evaluates historical data regarding the patient related to acute kidney injury, the historical data including historical renal data and past incidents of acute kidney injury.

In addition to other aspects, or in the alternative, another aspect can include wherein the data used by the evaluation circuit includes pharmaceutical usage data.

In addition to other aspects, or in the alternative, another aspect can include wherein the data used by the evaluation circuit includes medical procedural data.

In addition to other aspects, or in the alternative, another aspect can include wherein the evaluation circuit assigns an index of severity after determining whether acute kidney injury has occurred.

In addition to other aspects, or in the alternative, another aspect can include wherein externally gathered data is conveyed to the evaluation circuit via the telemetry circuit.

In addition to other aspects, or in the alternative, another aspect can include the externally gathered data being generated by an in-home external patient device.

In addition to other aspects, or in the alternative, another aspect can include the externally gathered data being generated in a clinical environment.

In addition to other aspects, or in the alternative, another aspect can include the evaluation circuit configured to generate a recommended therapeutic response after determining that acute kidney injury has occurred.

In addition to other aspects, or in the alternative, another aspect can include the recommended therapeutic response is dependent on whether the acute kidney injury is caused by pre-renal or intrinsic renal factors.

In addition to other aspects, or in the alternative, another aspect can include the recommended therapeutic response is accompanied by information indicating whether the acute kidney injury is caused by pre-renal or intrinsic renal factors.

In some examples, methods are included such as a method of detecting acute kidney injury. The method can include collecting renal data with a sensor circuit, the renal data including at least one of systemic renal data, direct renal data, urinary tract data, and renal-relevant extracorporeal data. The method can include storing the renal data in a memory circuit. The method can include assessing renal status with an evaluation circuit, wherein assessing includes receiving renal data from at least one of the sensor circuit and the memory circuit. The method can include determining whether acute kidney injury has occurred or is likely to occur by comparing the renal data to at least one of threshold values, personal historical values, patient population values and patterns indicative of acute kidney injury. The method can also include initiating a warning with the evaluation circuit if acute kidney injury has occurred or is likely to occur.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

Figure 1:
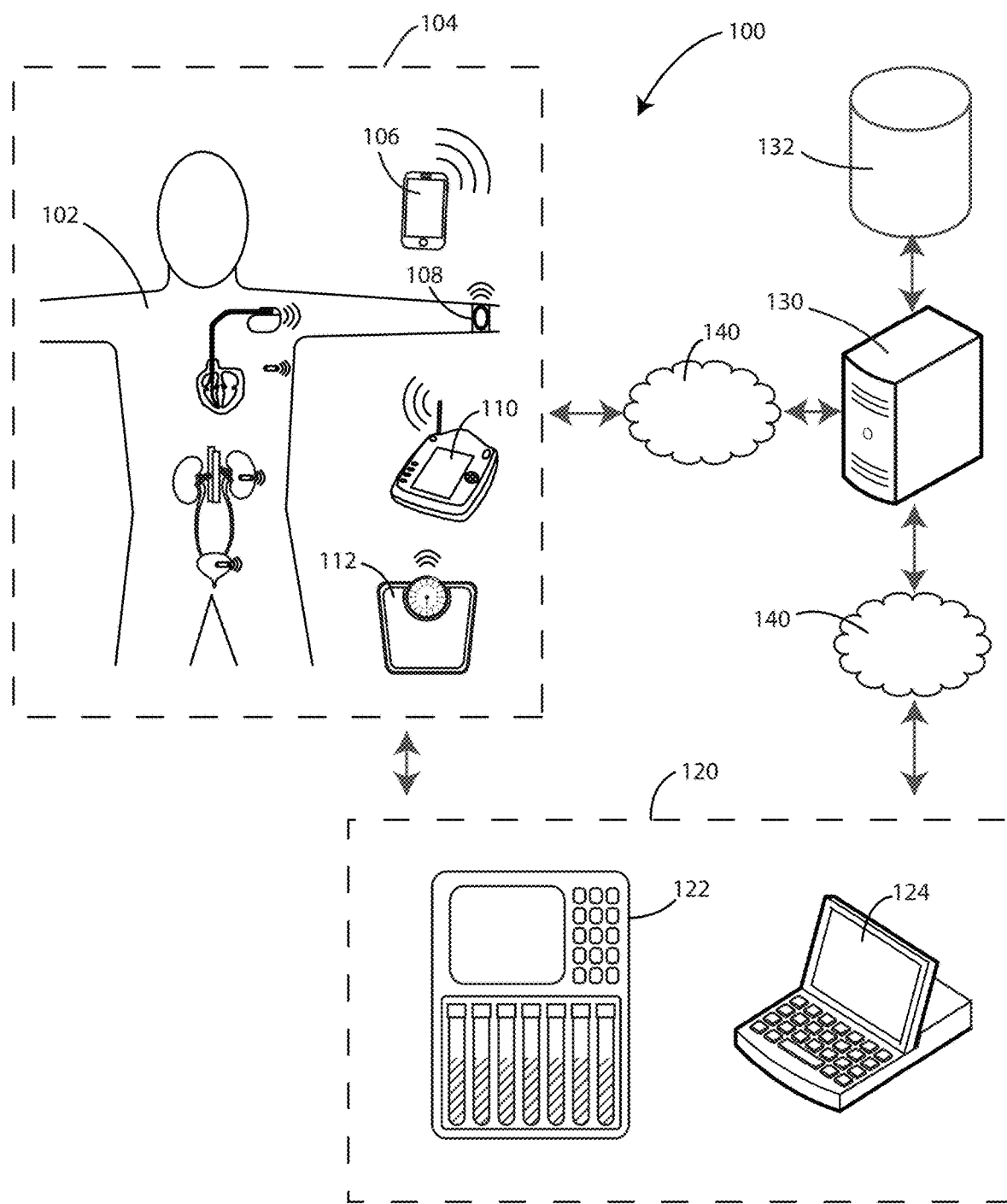
FIG. 1 is a schematic view of various components of a system in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

The embodiments described herein are not intended to be exhaustive or to limit the invention to the precise forms disclosed in the following detailed description. Rather, the embodiments are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As referenced above, acute kidney injury (AKI) is the abrupt loss of kidney function, resulting in the retention of urea and other nitrogenous waste products and in the dysregulation of extracellular volume and electrolytes. AKI can be fatal and requires immediate and intensive treatment. However, if treated appropriately and in time, AKI is often reversible.

Various embodiments of systems and methods herein can be used to identify AKI at a time point early enough so that the condition can still be effectively treated and in some cases reversed. In various embodiments, AKI can be detected at a time point that earlier than when tradition methods of diagnosing AKI would indicate that AKI is present. Various embodiments herein can also be used to predict the risk of AKI.

In some embodiments, a monitoring system to detect acute kidney injury is included. The monitoring system can include a sensor circuit configured to collect renal data including at least one of systemic renal data, direct renal data, urinary tract data, and renal-relevant extracorporeal data. The term "systemic renal data", as used herein, shall refer to data gathered outside of the renal and urinary systems but bearing on the functioning of the renal system of a patient. Non-limiting examples of systemic renal data are shown below in Table 1. The term "direct renal data", as used herein, shall refer to data gathered directly from or directly about the functioning of the renal system of a patient. Non-limiting examples of direct renal data are shown below in Table 1. The term "urinary tract data", as used herein, shall refer to data gathered from or about the urinary tract of a patient. Non-limiting examples of urinary tract data are shown below in Table 1. The term "renal-relevant extracorporeal data", as used herein, shall refer to extracorporeal data that is relevant to the functioning of the renal system of a patient, but is not systemic renal data, direct renal data, or urinary tract data. Non-limiting examples of renal-relevant extracorporeal data are shown below in Table 1.

TABLE 1

| Source of Information | Examples |
| --- | --- |
| Systemic Renal Data | Volumetric Status (Hydration Status); Blood Pressure; Hemodynamic Status (heart rate, respiratory rate, heart sounds (S1-S4), stroke volume); Glucose; Temperature; Inflammatory Markers (CRP, IL-6, IL-8, IL-10, serum amyloid A, WBC, fibrinogen, TNF-alpha) |
| Direct Renal Data | Serum Creatinine; Blood Urea Nitrogen (BUN); Electrolytes (plasma sodium, potassium, calcium, chloride, magnesium, phosphate); Anion Gap; $CO_2$; Serum Albumin; Serum Protein; Glomerular Filtration Rate; Renal Blood Pressure; Renal Blood Flow |
| Urinary Tract Data | Urine Biomarkers; Urine Osmolality; Urine Pressure; Urine Volume; Urine Flow; Urine Specific Biomarkers (creatinine, sodium, albumin, protein, bacteria, myoglobin, nitrates, pH, glucose, urinary casts) |
| Renal-Relevant Extra-Corporeal Data | Data Regarding Medications of Patient: (e.g., ACE inhibitors and angiotensin receptor blockers (ARBs), aminoglycosides, amphotericin B, and radiologic contrast agents; nephrotoxic medications); Information about Recent Procedures of Patient: (e.g., recent use of procedures radiologic contrast agents); Information about Recent Diagnoses of Patient: (e.g., recent AKI diagnosis; Recent Hospital Admission); Information about Previous AKI Development and Treatment Response for Patient (e.g., patient AKI and/or marker value history) Comorbidities: (e.g. chronic kidney disease, heart failure, hypertension, diabetes, arteriosclerosis) |

It will be appreciated that in some embodiments the data above can be used as absolute values. For example, urine volume can be evaluated as an absolute value. An example of this would be urine volume of 5.0 ml per hour. In other cases, the data above can be used as relative values. The value can be made relative by normalizing it against other data such as average values for that particular patient, average values for a patient population, or the like. In various embodiments, the comparison data can be indexed by weight, age, or other values. In some embodiments, the data can be compared with previous or baseline data to indicate trends. For example, the particular renal data (for example, urine volume) is decreasing, increasing, or staying the same.

In some embodiments, various pieces of data can be turned into binary indicators through the comparison of the value (absolute or relative) to a threshold or other fixed value. For example, urine volume less than 0.5 ml/kg per hour for six hours for a patient can be a positive indicator of an AKI event. In some embodiments, using creatinine as a specific example, an increase in serum creatinine (SCr) of ≥0.3 mg/di (≥26.5 µmol/l) within 48 hours can serve as positive indicator of an AKI event. As another specific example, an increase in SCr to ≥1.5 times baseline, occurring within the prior 7 days can serve as positive indicator of an AKI event. In some embodiments, a glomerular filtration rate (GFR) decrease by 25 percent can serve as a positive indicator of an AKI event.

The monitoring system can also include a memory circuit to store collected renal data. In some embodiments the memory circuit can store baseline values for a patient across the various categories of renal data. By way of example, the memory circuit can store baseline data for a particular patient across one or more of the categories of systemic renal data, direct renal data, urinary tract data, and renal-relevant extracorporeal data. In some embodiments, the memory circuit stores baseline data for a particular patient across all of the categories of systemic renal data, direct renal data, urinary tract data, and renal-relevant extracorporeal data.

The monitoring system can also include an evaluation circuit configured to receive the renal data from at least one of the sensor circuit and the memory circuit and assess renal status. In some embodiments, the evaluation circuit can further process or manipulate data. By way of example, in some embodiments, the evaluation circuit can estimate at least one of glomerular filtration rate (GFR) and fractional excretion of filtered sodium. It will be appreciated that glomerular filtration rate can be estimated in various ways. In some embodiments, GFR can be calculated using a patient's age, race, serum creatinine, and gender. GFR can be estimated using the CKD-EPI creatinine equation, the Modification of Diet in Renal Disease (MDRD) Study equation, the Mayo Quadratic Formula, the Cockcroft and Gault equation, or the like. In some embodiments, GFR can also be estimated using serum cystatin C values, age and sex. Exemplary techniques for estimating GFR are described in US20100121220, US20140235503, and US20160003810, the content of which is herein incorporated by reference. Fractional excretion of filtered sodium is the percentage of the sodium filtered by the kidney which is excreted in the urine. It will be appreciated that fractional excretion of filtered sodium can be estimated in various ways including by, evaluating plasma and urine sodium. The fractional excretion of sodium is equal to the clearance of sodium divided by the glomerular filtration rate. The monitoring system can also include a telemetry circuit in electronic communication with at least one of the sensor circuit and the evaluation circuit.

In some embodiments, the evaluation circuit can determine whether acute kidney injury has occurred or is likely to occur by comparing the renal data to at least one of threshold values, personal historical values (baseline), patient population values and patterns indicative of acute kidney injury. In some embodiments the evaluation circuit can be configured to initiate a warning notification if acute kidney injury has occurred or is likely to occur.

In some cases the accuracy and/or sensitivity of the system can be enhanced by including more data sources in the evaluation. As such, in some embodiments, the sensor circuit collects at least two of systemic renal data, direct renal data, urinary tract data and renal-relevant extracorporeal data. In some embodiments, the sensor circuit collects at least three of systemic renal data, direct renal data, urinary tract data and renal-relevant extracorporeal data. In some embodiments, the sensor circuit collects all four of systemic renal data, direct renal data, urinary tract data and renal-relevant extracorporeal data.

The components of the system can be together in one device or distributed across separate devices that can be in communication with one another. One or more components of the system can be implanted. In some embodiments, all components of the system are implanted. One or more components of the system can be external. In some embodiments, all components of the system are external. In some embodiments, the system can include both implanted components and external components. In some embodiments, at least one of the sensor circuit, memory circuit, evaluation circuit and telemetry circuit are at least partially housed in an implanted device. In some embodiments, at least one of the sensor circuit, memory circuit, evaluation circuit and telemetry circuit are housed in a wearable device. In some embodiments, the telemetry circuit conveys renal data to the evaluation circuit, and the evaluation circuit is located remotely from the sensor circuit. In some embodiments, the telemetry circuit conveys the renal data to a remotely located server containing the evaluation circuit.

In some embodiments, the evaluation circuit is configured to execute a pattern matching algorithm to classify a patient. Many techniques of classifying the patient can be used. As one example, a database can be maintained of patient information including renal data over time as well as information regarding when these patients suffered AKI incidents and, in some cases, the severity of such incidents. In some cases, the patient data can also be temporally indexed such that snapshots of renal data at different time points can be treated as discrete data records for pattern matching purposes. This patient data can be divided into groups according to whether or not an AKI event was suffered and, in some cases, when that AKI event was suffered as a function of how long after the data snapshot the AKI event occurred. A pattern matching algorithm can then be used in order to take data from the patient being monitored and match it against the group of patient data that is most like the data from the patient being monitored. The patient can then be categorized according to which group his/her renal data matches most closely. Exemplary algorithms used for classification and/or comparison steps herein can include parametric and nonparametric statistical classification algorithms including, but not limited to, linear discriminant analysis, quadratic discriminant analysis, maximum entropy classification, decision trees, kernel estimation, neural network analysis, naïve Bayes classifiers, perceptron techniques, support vector machine approaches, and the like. Exemplary algorithms can also include clustering algorithms including deep learning methods, hierarchical clustering, K-means clustering, correlation clustering and kernel principal component analysis.

Various classifications can be applied. In some embodiments, the classifications can include:
1.) Currently suffering from acute renal injury,
2.) Imminently likely to suffer acute renal injury, and
3.) Not suffering from acute renal injury and not imminently likely to suffer acute renal injury.

In some embodiments, the evaluation circuit places the patient into a category indicative of the patient's risk of suffering an acute kidney injury. Various numbers of categories can be used. In some embodiments there are between 2 and 5 categories. In some embodiments, categories can include "at risk for AKI" and "not at risk for AKI". In some embodiments, categories can include "high risk for AKI", "moderate risk for AKI", and "low risk for AKI".

In some embodiments, instead of or in addition to classifications, the evaluation circuit calculates a risk index score indicative of the patient's risk of suffering an acute kidney injury. By way of example, a risk index score can be calculated by comparing the patient's present status against predetermined profiles of patients and integrating this data into a single score which is indicative of his/her risk of an AKI event. Such a risk index score can be calculated in various ways. In some embodiments, different types of renal data such as systemic renal data, direct renal data, urinary tract data and renal-relevant extracorporeal data can be compared against population data, thresholds, averages or the like that are specific for that type of renal data. For example, systemic renal data can be evaluated against thresholds specific for system renal data. Then values across the different types of renal data can be combined on either a weighted or non-weighted basis.

In some embodiments, externally gathered data is conveyed to the evaluation circuit via the telemetry circuit. In some embodiments, the externally gathered data is generated by an in-home external patient device.

In some embodiments, the evaluation circuit can be configured to categorize the type of causation for the AKI event. Causes of AKI are frequently classified as prerenal, intrinsic, or post-renal. Prerenal causes of AKI are those that decrease effective blood flow to the kidney. Sources of damage to the kidney itself are dubbed intrinsic causes. Post-renal causes of AKI are those resulting in urinary tract obstruction.

An AKI event can be categorized using various techniques. As an example, AKI events, recognized for example by the presence of increased creatinine levels or decreased urine output, can be classified according to their likely cause. For example, an AKI event can be classified as prerenal by detection of hypovolemia. In another example, an AKI event can be classified as intrinsic by detection of acute tubular necrosis based on various factors, including but not limited to, the presence or trends in proteins or blood in urine. In yet another example, an AKI event can be classified as post-renal by detection of urinary tract obstruction. The increased creatinine levels and decreased urinary output resulting from an AKI event can be detected by the system with a chemical sensor capable of measuring creatinine concentration and a urinary flow sensor respectively.

The hypovolemia associated with pre-renal AKI can be recognized by the system by the detection of one or more of hypotension, postural hypotension, decreased urine output, increased heart rate, increased cardiac contractility, increased respiratory rate and decreased weight. Hypotension can be measured by the system via an implanted or wearable blood pressure sensor. Increased respiration rate can be measured by the system via an implanted or wearable respiration sensor, for example an impedance-based sensor. Increased heart rate can be measured by the system via an implanted or wearable electrocardiogram sensor.

The acute tubular necrosis associated with intrinsic AKI can be recognized by the system by detection of prolonged hypertension or renal-toxic agents. Prolonged hypotension can be measured by the system via an implanted or wearable blood pressure sensor. Renal-toxic agents can be recognized by the system via connection to an electronic medical database containing recent pharmaceutical use by the patient including, for example, renal-toxic agents such as chemotherapeutic drugs, antibiotics and radiocontrast dyes.

The urinary tract obstruction associated with post-renal AKI can be recognized by the system by detection of increased pressure at one or more locations in the urinary tract, for example, in one or both ureters near their connection to the kidney or within the bladder. The increased pressure can be measured by the system via one or more pressure sensors. It will be appreciated that pressure sensors herein can be used to measure the pressure of any type of fluid such as blood, urine, or other fluids. The pressure sensor can include any type of pressure sensor, for example an electrical, mechanical, or optical sensor, which generates a signal in response to local pressure. By way of example, the pressure sensor can include devices such as those described in U.S. Pat. No. 6,237,398, the contents of which are herein incorporated by reference.

In some embodiments, the evaluation circuit can be configured to generate a recommended therapeutic response after determining that acute kidney injury has occurred. In some embodiments, the recommended therapeutic response can be dependent on whether the acute kidney injury is caused by pre-renal, intrinsic renal or post-renal factors. In some embodiments, the recommended therapeutic response can be accompanied by information indicating whether the acute kidney injury is caused by pre-renal, intrinsic renal or post-renal factors. Exemplary therapeutic actions are described below in Table 2. However, it will be appreciated that this is only provided by way of illustration and other therapeutic interventions are contemplated herein. In addition to pharmacological therapy, device based therapies such as baroreceptor modulation, spinal cord stimulation, renal denervation/stimulation may be advantageously modified to affect pre-renal, renal or post-renal function. In some embodiments, an instruction can be sent from the system to a device that can deliver device based therapies such as baroreceptor modulation, spinal cord stimulation, and/or renal denervation/stimulation.

TABLE 2

| Causation Category | Specific Causation | Therapeutic Action |
| --- | --- | --- |
| Pre-Renal | Volume Depletion | Intravenous fluids<br>Decrease or discontinue diuretic therapy<br>If due to blood loss treat cause of blood loss<br>If due to diarrhea treat cause of diarrhea |
| Pre-Renal | Insufficient Cardiac Output | Intravenous fluids<br>If due to blood loss treat cause of blood loss<br>Increase or initiate inotrope/vasopressor therapy (e.g. norepinephrine, dobutamine) |
| Pre-Renal | Systemic Vasodilation | Decrease or discontinue vasodilation therapy<br>Increase or initiate vasopressor (vasoconstriction) therapy |
| Pre-Renal | Afferent Arteriolar Vasoconstriction | Increase or initiate vasodilation therapy<br>Decrease or discontinue vasopressor (vasoconstriction) therapy |
| Intrinsic Renal | Renal Arterial Stenosis | Renal artery angioplasty<br>Renal artery bypass<br>Increase or initiate hypertension or hyperlipidemia therapy |
| Post-Renal | Urinary Tract Blockage | Antibiotic therapy<br>Insertion of a catheter (urethral or suprapubic)<br>Insertion of a ureteral stent |

Approximately 70% instances of AKI are due to prerenal conditions, so it is clinically important to manage this cause of AKI. Prerenal AKI is most often treated with either or both of administration of intravenous fluids to reestablish normal fluid status and/or administration of inotropes such as norepinephrine and dobutamine to increase cardiac output. If the system detects AKI, classifies it as prerenal AKI and determines the patient is not hypovolemic, the system can initiate and/or modulate delivery of inotrope therapy via an implantable or wearable drug pump. Other types of therapy that can be initiated and/or modulated include, but are not limited to, vasopressors, inodilators, diuretics, other types of hypertension therapeutics, hyperlipidemia agents, and the like.

If the system detects AKI and classifies it as intrinsic or post-renal, it can instruct the patient (such as through an audio and/or visual alert from an external device) to go to a medical facility for immediate medical therapy. Further, if the system detects AKI, classifies it as prerenal and detects hypovolemia, it can instruct the patient (such as through an audio and/or visual alert from an external device) to go to a medical facility for immediate medical therapy.

Referring now to FIG. 1, a schematic view is shown of various possible components of a system 100 in accordance with various embodiments herein. The system 100 can include external patient specific devices within a patient environment 104 including, but not limited to, a smart phone 106, a wearable device 108, a patient communicator 110 (or patient management device), and a patient-specific data gathering device 112, such as a weight scale. The patient environment 104 can also include devices implanted within the patient 102 (discussed in greater detail with respect to FIGS. 2-3 below). An exemplary patient management system is the LATITUDE® patient management system, commercially available from Boston Scientific Corporation, Natick, Mass. Aspects of an exemplary patient management system are described in U.S. Pat. No. 6,978,182, the content of which is herein incorporated by reference.

The system 100 can also include devices within a clinical environment 120 including, but not limited to, a programmer device 124 that can be used to send data to and/or receive data from implanted devices as well as from other devices across a network. The clinical environment 120 can also include diagnostic test systems 122 that can provide data regarding chemical analytes of patients. Devices and systems in the clinical environment 120 can communicate with devices and systems in the patient environment 104 for the exchange of data.

The system 100 can also include a computing device such as a server 130 (real or virtual). In some embodiments, the server 130 can be located remotely from the patient environment 104 and/or the clinical environment 120. The server 130 can be in data communication with a database 132. The database 132 can be used to store various patient information, such as that described herein. In some embodiments, the database can specifically include an electronic medical database containing data regarding recent pharmaceutical use by a patient including, but not limited to, renal-toxic agents such as chemotherapeutic drugs, antibiotics and/or radiocontrast dyes. In some embodiments, the database can include data used by an evaluation circuit such as pharmaceutical usage data and medical procedural data. In some embodiments, the database can include historical data regarding the patient related to acute kidney injury, the historical data including historical renal data and past incidents of acute kidney injury.

The server 130 can be in data communication with the patient environment 104 and/or the clinical environment 120 through a network such as the Internet or another public or private data network including packet switched data networks or non-packet switched data networks. In some embodiments, the server 130 can be located in proximity to the patient environment 104 and/or the clinical environment 120.

Figure 2:
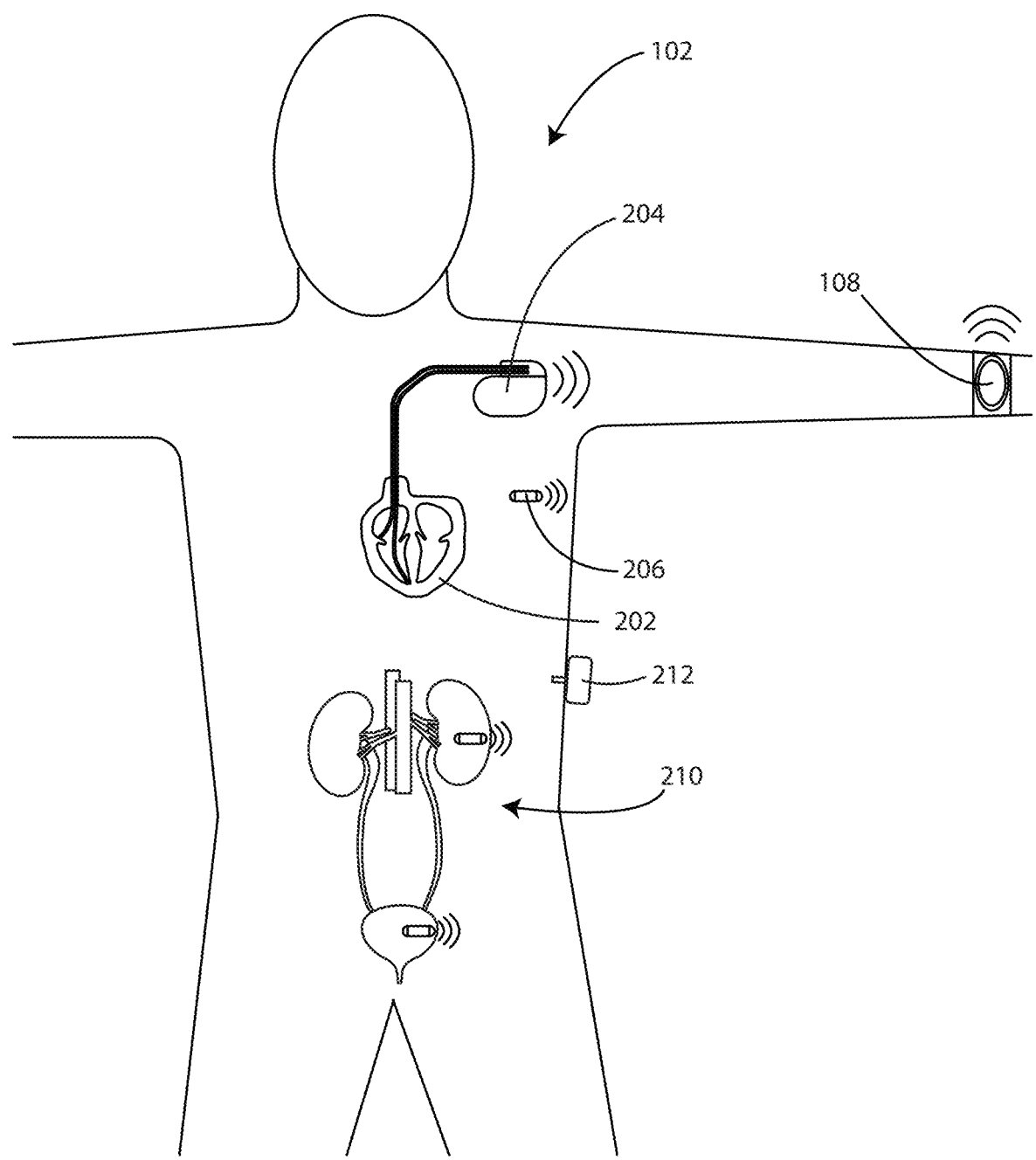
FIG. 2 is a schematic view of a patient and various devices associated with the patient.

Referring now to FIG. 2, a schematic view is shown of patient 102 and various devices associated with the patient 102. The patient 102 can have various implanted devices and various external devices, including but not limited to wearable devices. The patient 102 can utilize a wearable device 108. While the wearable device 108 in FIG. 2 is on the patient's 102 wrist, it will be appreciated that this is merely one example and the device can also be worn on other parts of the patient 102. The wearable or other external devices can provide various functionality. In some embodiments, the wearable or other external device can be used to provide alerts to the patient and/or to care providers located in the same place as the patient or remotely. Alerts can take various forms. In some embodiments, the alert can be an audio and/or visual alert. In some embodiments, the wearable or other external device can be used to display information to the patient and/or to care providers. In some embodiments, the wearable device(s) can include sensors, such as any of the types of sensors described herein.

In some embodiments the patient 102 can include an implanted cardiac device 204. In some embodiments, the implanted cardiac device 204 can be connected to leads for sensing and/or electrical stimulation that can be disposed in or near the patient's heart 202. The implanted cardiac device 204 can include various sensors and/or can be connected to various sensors. In some embodiments, an implanted monitoring/sensing device 206 can be implanted within the patient 102. Further details of an exemplary implanted monitoring/sensing device 206 are provided below with respect to FIG. 4 and the accompanying description. However, it will be appreciated that this is merely one example of an implanted device that can be used with systems herein. The patient's renal-urinary system 210 can also include various sensors/devices. An implantable or wearable drug pump 212 can also be included. The implantable or wearable drug pump (or drug infusion device) 212 can be configured to provide inotrope therapy, or provide other types of therapeutic active agents. One exemplary wearable drug pump is described in U.S. Pat. No. 6,589,229, the content of which is herein incorporated by reference.

Figure 3:
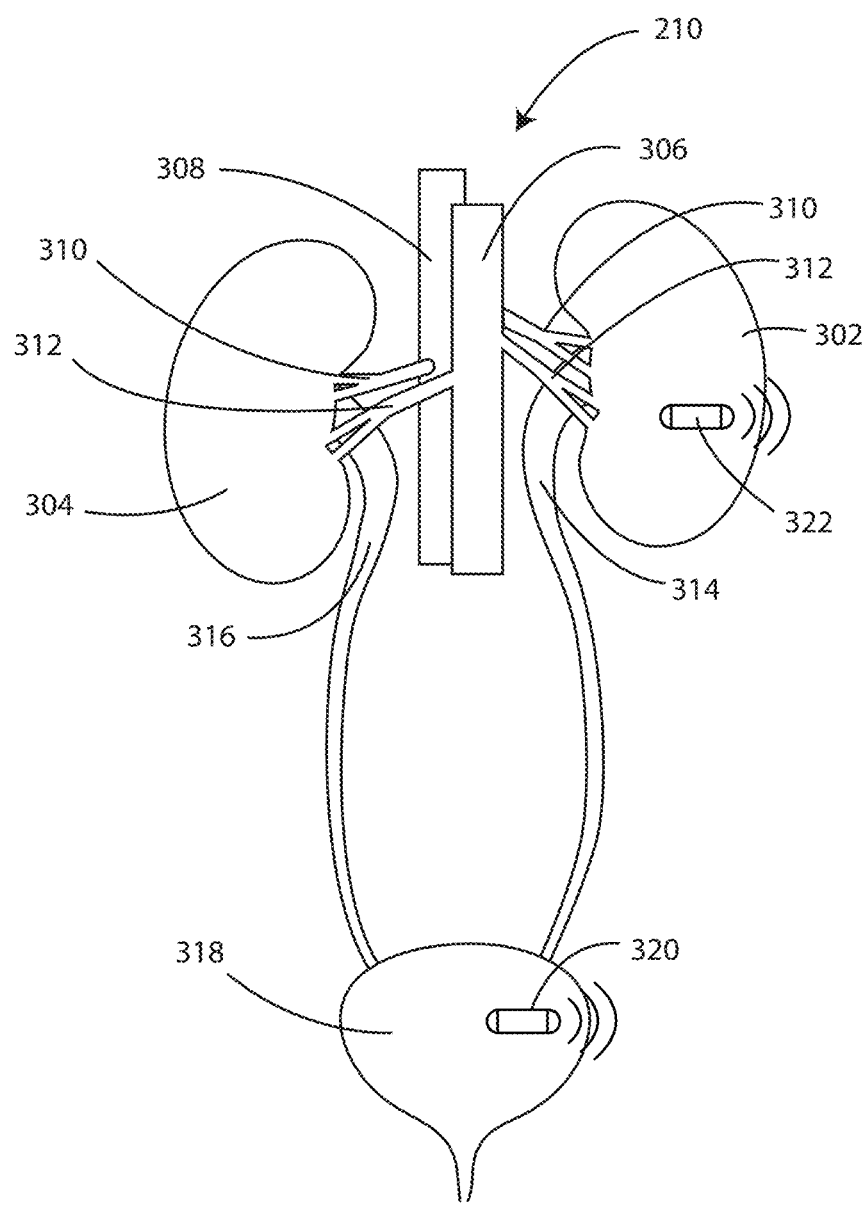
FIG. 3 is a schematic view of a patient's renal-urinary system and various devices associated therewith in accordance with various embodiments herein.

Referring now to FIG. 3, a schematic view of the patient's renal-urinary system 210 is shown in accordance with various embodiments herein. The renal-urinary system 210 can include a left kidney 302 and a right kidney 304. The left kidney 302 and the right kidney 304 can be connected to the abdominal aorta 306 through vessels 312. The left kidney 302 and the right kidney 304 can be connected to the inferior vena cava 308 through vessels 310. The left kidney 302 and right kidney 304 can be in fluid communication with the bladder 318 via the left ureter 314 and right ureter 316 respectively. Various sensors can be disposed in or about the renal-urinary system 210 in order to provide data regarding the renal-urinary system 210. By way of example, a sensor/monitor device 322 can be disposed on or in the left kidney 302 and/or the right kidney 304 (shown here only on the left kidney 302). A sensor/monitor device 320 can be disposed on or in the bladder 318. In some embodiments, a sensor/monitor device can also be disposed on or in the ureters. In some embodiments, the sensor/monitor device 320 can include chemical sensing hardware. Exemplary chemical sensing hardware is described in greater detail below. In some embodiments, the sensor/monitor device 320 can include flow sensing hardware. In some embodiments, the flow sensing hardware can specifically be urinary flow sensing hardware. It will be appreciated that there are various approaches to measuring flow of a fluid. Exemplary flow sensors can include differential pressure based flow meters, orifice plate, Venturi tubes, flow nozzle, calorimetric flow meters, velocity based flow meters, turbine flow meters, ultrasonic Doppler flow meters, positive displacement based flow meters, mass based flow meters, and the like.

Figure 4:
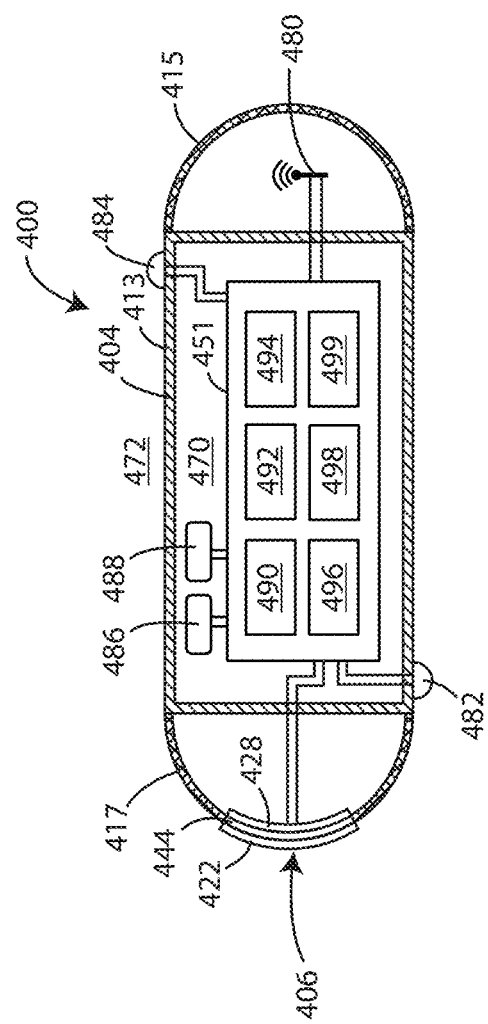
FIG. 4 is a schematic cross-sectional view of an exemplary sensor/monitor device.

Embodiments of systems herein can include sensor/monitor devices. Referring now to FIG. 4, a schematic cross-sectional view of an exemplary sensor/monitor device 400 is shown in accordance with various embodiments herein. The sensor/monitor device 400 includes a housing 404. The housing 404 of the sensor/monitor device 400 can include various materials such as metals, polymers, ceramics, and the like. In some embodiments, the housing 404 can be a single integrated unit. In other embodiments, the housing 404 can include a main segment 413 along with appendage segments 415 and 417. In one embodiment, the housing 404, or one or more portions thereof, is formed of titanium. In some embodiments, one or more segments of the housing 404 can be hermetically sealed. In some embodiments, the main segment 413 is formed of a metal and the appendage segments 415 and 417 are formed from a polymeric material.

The housing 404 defines an interior volume 470 that in some embodiments is hermetically sealed off from the area 472 outside of the sensor/monitor device 400. The sensor/monitor device 400 can include circuitry 451. The circuitry 451 can include various components, such as components 490, 492, 494, 496, 498, and 499. In some embodiments, these components can be integrated, and in other embodiments, these components can be separate. In some embodiments, the components can include one or more of a microprocessor, memory circuitry (such as random access memory (RAM) and/or read only memory (ROM)), recorder circuitry, telemetry circuitry, sensor and/or sensor interface circuitry, power supply circuitry (which can include one or more batteries), normalization circuitry, control circuitry, evaluation circuitry, and the like. In some embodiments, recorder circuitry can record the data produced by the chemical sensor and record time stamps regarding the same. In some embodiments, the circuitry can be hardwired to execute various functions while in other embodiments, the circuitry can be implemented as instructions executing on a microprocessor or other computation device.

The sensor/monitor device 400 can include, for example, an electrical field sensor that is configured to generate a signal corresponding to cardiac electric fields. The electrical field sensor can include a first electrode 482 and a second electrode 484. In some embodiments, the housing 404 itself can serve as an electrode. The electrodes can be in communication with the electrical field sensor. The electrical field sensor can include a circuit in order to measure the electrical potential difference (voltage) between the first electrode 482 and the second electrode 484. The electrical field sensor can include a circuit in order to measure the impedance between the first electrode 482 and the second electrode 484. The sensor/monitor device 400 can also include an antenna 480, to allow for unidirectional or bidirectional wireless data communication.

The sensor/monitor device 400 can also include a chemical sensor 406. In the embodiment shown in FIG. 4, the chemical sensor is an optical chemical sensor. However, in other embodiments, the chemical sensor can be a potentiometric chemical sensor. The chemical sensor 406 can specifically include a chemical sensing element 422, an optical window 444, and an electro-optical module 428. The electro-optical module 428 can be in electrical communication with the circuitry 451 within the interior volume 470, and in some embodiments, the circuitry 451 is configured to selectively activate the chemical sensor 406. The chemical sensor 406 can be configured to be chronically implanted.

The chemical sensor 406 can include an electro-optical module 428 coupled to the optical window 444. The electro-optical module 428 can specifically include one or more optical excitation assemblies. Each optical excitation assembly can include various light sources such as light-emitting diodes (LEDs), vertical-cavity surface-emitting lasers (VCSELs), electroluminescent (EL) devices, or the like. The electro-optical module 428 can also include one or more optical detection assemblies. Each optical detection assembly can include one or more photodiodes, avalanche photodiodes, a photodiode array, a photo transistor, a multi-element photo sensor, a complementary metal oxide semiconductor (CMOS) photo sensor, or the like.

The chemical sensing element 422 can be disposed on the optical window 444. The chemical sensing element 422 can be configured to detect a physiological analyte by exhibiting an optically detectable response to the physiological analyte. Specific examples of physiological analytes are discussed in greater detail below. In operation, analytes of interest from the in vivo environment can diffuse into the chemical sensing element 422 causing a detectable change in the optical properties of the chemical sensing element 422. Light can be generated by the electro-optical module 428 and can pass through the optical window 444 and into the chemical sensing element 422. Light can then either be preferentially reflected from or re-emitted by the chemical sensing element 422 proportional to the sensed analyte and pass back through the optical window 444 before being received by the electro-optical module 428. Various aspects of exemplary chemical sensors are described in greater detail in U.S. Pat. No. 7,809,441, the content of which is herein incorporated by reference in its entirety.

In some embodiments the chemical sensing element 422 is located in a fluid such as blood, interstitial fluid, urine, lymph or chyle and senses analytes in the fluid. In other embodiments, the chemical sensing element 422 is located in a solid tissue such as muscle, fat, bone, bone marrow, organ tissues (e.g. kidney, liver, brain, lung, etc.) and senses analytes in the solid tissue.

Figure 5:
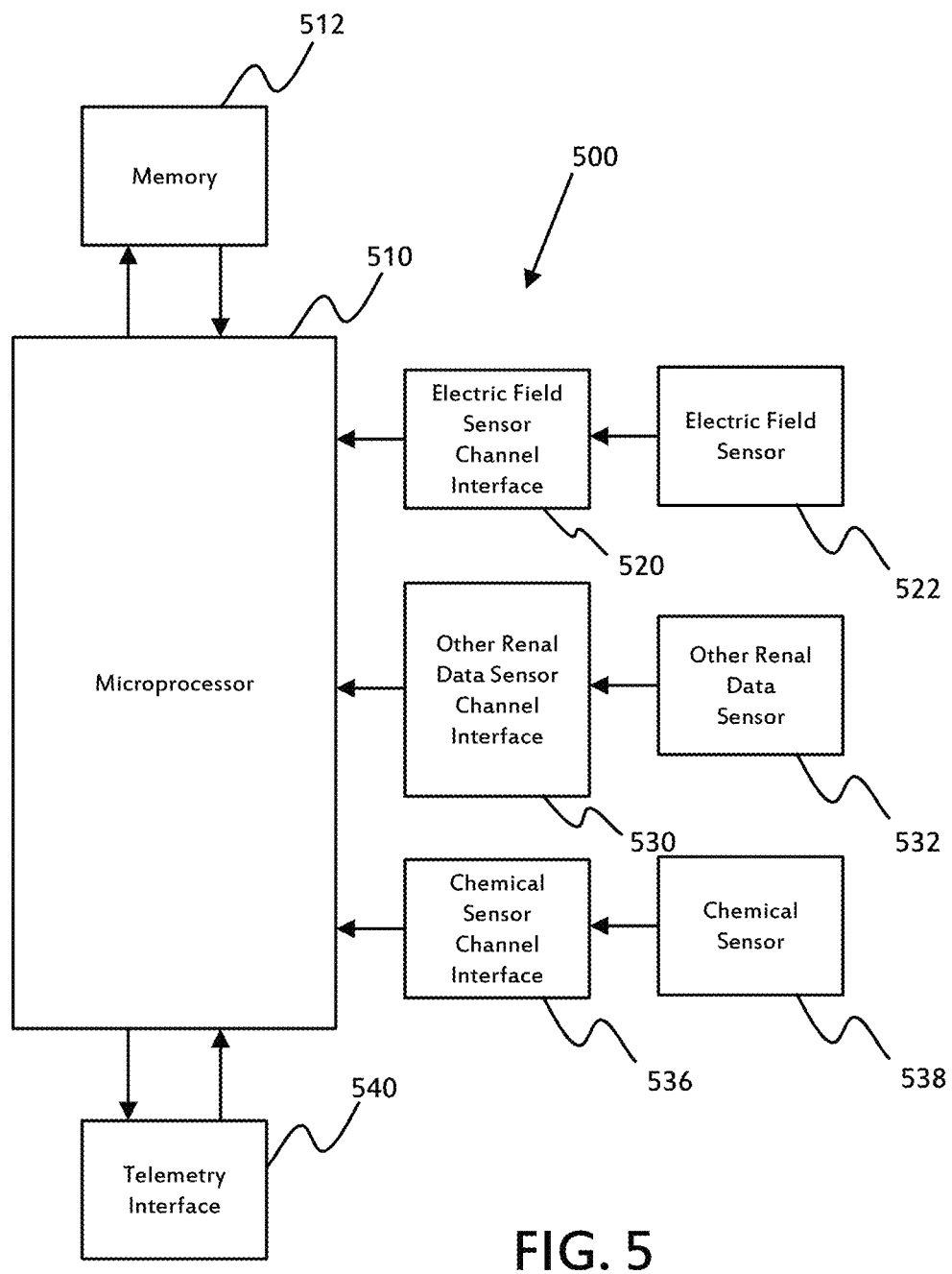
FIG. 5 is a schematic view of elements of a sensor/monitor device in accordance with various embodiments herein.

Elements of various devices that can be used as part of systems herein are shown in FIG. 5. However, it will be appreciated that some embodiments devices used herein with systems can include additional elements beyond those shown in FIG. 5. In addition, some embodiments of devices used with systems herein may lack some elements shown in FIG. 5. The device 500 (which can be implanted or external) can gather renal information through one or more sensing channels. A microprocessor 510 can communicate with a memory 512 via a bidirectional data bus. The memory 512 can include read only memory (ROM) or random access memory (RAM) for program storage and RAM for data storage.

The device 500 can include one or more electric field sensors 522 (in some cases, electrodes) and an electric field sensor channel interface 520 (for measuring impedance, electrical potential, or other electrical properties) which can communicate with a port of microprocessor 510. The device 500 can also include one or more other renal data sensor(s) 532 and other renal data sensor channel interface 530 which can communicate with a port of microprocessor 510.

The other renal data sensors (implantable, wearable, or non-wearable external) can include, but are not limited to, one or more of a posture sensor, activity sensor, a respiration sensor, pressure sensor (including blood pressure and/or urine pressure), flow sensor, impedance sensor, and any of the other types of sensors discussed herein.

The device 500 can also include a chemical sensor 538 and a chemical sensor channel interface 536 which can communicate with a port of microprocessor 510. The sensor channel interfaces 520, 530 and 536 can include various components such as analog-to-digital converters for digitizing signal inputs, sensing amplifiers, registers which can be written to by the control circuitry in order to adjust the gain and threshold values for the sensing amplifiers, and the like. A telemetry interface (or telemetry circuit) 540 is also provided for communicating with other devices of a system such as a programmer, a home-based unit and/or a mobile unit (e.g., a cellular phone).

Figure 6:
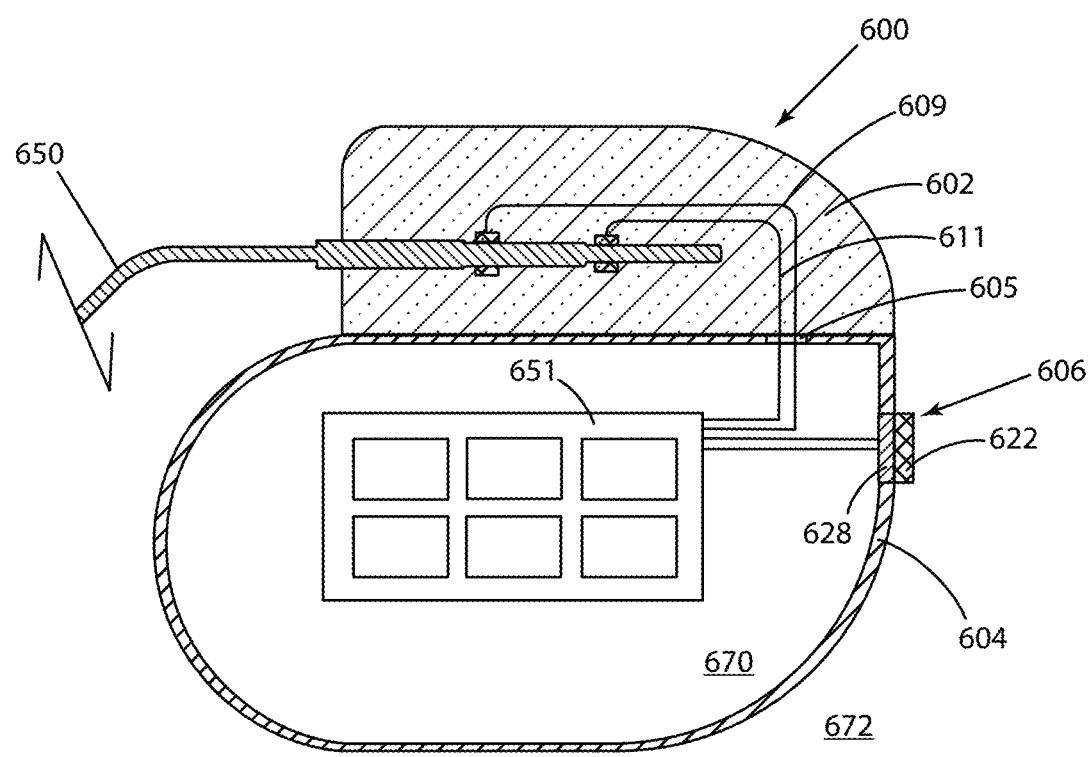
FIG. 6 is a schematic cross-sectional view of an implantable medical device in accordance with various embodiments herein.

Renal data herein can also be gathered by various other types of implantable medical devices, including but not limited to implantable cardiac devices. Referring now to FIG. 6, a schematic cross-sectional view of an implantable medical device 600 is shown in accordance with various embodiments herein. The implantable medical device 600 includes a header assembly 602 and a housing 604. The housing 604 of the implantable medical device 600 can include various materials such as metals, polymers, ceramics, and the like. In one embodiment, the housing 604 is formed of titanium. The header assembly 602 can be coupled to one or more electrical stimulation leads 650. The header assembly 602 serves to provide fixation of the proximal end of one or more leads and electrically couples the leads to components within the housing 604. The header assembly 602 can be formed of various materials including metals, polymers, ceramics, and the like.

The housing 604 defines an interior volume 670 that is hermetically sealed off from the volume 672 outside of the device 600. Various electrical conductors 609, 611 can pass from the header 602 through a feed-through structure 605, and into the interior volume 670. As such, the conductors 609, 611 can serve to provide electrical communication between the electrical stimulation lead 650 and control circuitry 651 disposed within the interior volume 670 of the housing 604. The control circuitry 651 can include various components such as a microprocessor, memory (or memory circuit) (such as random access memory (RAM) and/or read only memory (ROM)), a telemetry module, electrical field sensor and stimulation circuitry, a power supply (such as a battery), and an optical sensor interface channel, amongst others. The control circuitry 651 can include the evaluation circuitry in various embodiments herein.

The implantable medical device 600 can incorporate, for example, an electrical field sensor that is configured to generate a signal corresponding to cardiac electric fields. The electrical field sensor (for measuring impedance, electrical potential, or other electrical properties) can include a first electrode and a second electrode. The electrodes of the electrical field sensor can be the same electrodes used to provide electrical stimulation or can be different electrodes. In some embodiments, one or more electrodes can be mounted on one or more electrical stimulation leads 650. In some embodiments, the housing 604 can serve as an electrode. The electrodes can be in communication with the electrical field sensor and stimulation circuitry. The electrical field sensor can include a circuit (such as within control circuitry 651) in order to measure the electrical potential difference (voltage) between the first electrode and the second electrode. In some embodiments, the data from the electrical field sensor can be used to generate an electrocardiogram.

The implantable medical device 600 can also include a chemical sensor 606. In the embodiment shown in FIG. 6, the chemical sensor 606 is a potentiometric chemical sensor. The chemical sensor 606 can specifically include a receptor module 622, and a transducer module 628. The transducer module 628 can be in electrical communication with the circuitry 651 within the interior volume 670, and in some embodiments, the control circuitry 651 is configured to selectively activate the chemical sensor 606. The chemical sensor 606 can be configured to be chronically implanted.

The chemical sensor 606 can be configured to detect a physiological analyte by exhibiting an electrical signal response to the physiological analyte. In operation, analytes of interest from the in vivo environment can contact the receptor module 622 causing a detectable change in the electrical properties of the same. The transducer module 628 can then be used to process and/or propagate the signal created by the receptor module 622. While medical device 600 is described as being implantable, it will be appreciated that some or all of the same components and functionality can be included in an external and/or wearable medical device.

Figure 7:
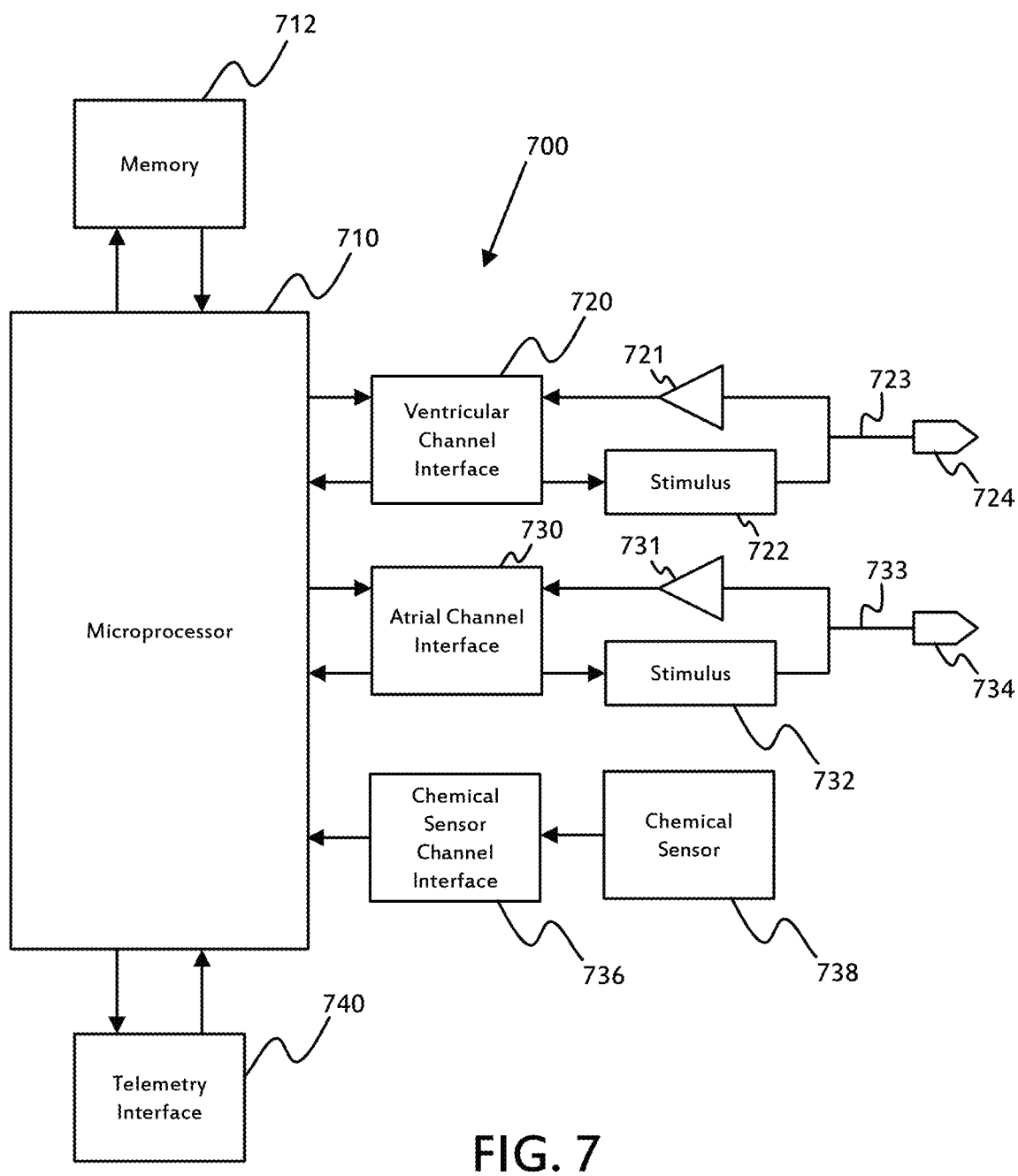
FIG. 7 is a schematic view of elements of an implantable medical device in accordance with some embodiments herein.

Elements of some embodiments of an implantable medical device that can be part of systems herein are shown in FIG. 7. However, it will be appreciated that some embodiments can include additional elements beyond those shown in FIG. 7. In addition, some embodiments may lack some elements shown in FIG. 7. The medical device 700 can sense cardiac events through one or more sensing channels and can output pacing pulses to the heart via one or more pacing channels in accordance with a programmed pacing mode. A microprocessor 710 communicates with a memory 712 via a bidirectional data bus. The memory 712 typically comprises read only memory (ROM) or random access memory (RAM) for program storage and RAM for data storage.

The implantable medical device can include atrial sensing and pacing channels comprising at least a first electrode 734, a lead 733, a sensing amplifier 731, an output circuit to provide a stimulus 732, and an atrial channel interface 730 which can communicate bidirectionally with a port of microprocessor 710. In this embodiment, the device 700 also has ventricular sensing and pacing channels comprising at least a second electrode 724, a lead 723, a sensing amplifier 721, an output circuit to provide a stimulus 722, and ventricular channel interface 720. For each channel, the same lead and electrode are used for both sensing and pacing. The channel interfaces 720 and 730 include analog-to-digital converters for digitizing sensing signal inputs from the sensing amplifiers and registers which can be written to by the control circuitry in order to output pacing pulses, change the pacing pulse amplitude, and adjust the gain and threshold values for the sensing amplifiers. The implantable medical device 700 can also include a chemical sensor 738 and a chemical sensor channel interface 736. A telemetry interface 740 is also provided for communicating with an external programmer or another implanted medical device.

Methods

Various methods are included herein. For example, various operations of devices and circuits described above can be performed as a part of a method. By way of further example, methods herein can include, but are not limited to, methods of monitoring for AKI, methods of detecting AKI, methods of tracking baseline renal data, methods of making an AKI monitoring system, methods of using an AKI monitoring system, and the like. In a particular embodiment, a method of detecting acute kidney injury is included. The method can include collecting renal data with a sensor circuit. The renal data can include at least one of systemic renal data, direct renal data, urinary tract data, and renal-relevant extracorporeal data. In an embodiment, the method can include storing the renal data in a memory circuit. In an embodiment, the method can include assessing renal status with an evaluation circuit, wherein assessing includes receiving renal data from at least one of the sensor circuit and the memory circuit. In an embodiment, the method can include determining whether acute kidney injury has occurred or is likely to occur by comparing the renal data to at least one of threshold values, personal historical values, patient population values and patterns indicative of acute kidney injury. The method can further include initiating a warning with the evaluation circuit if acute kidney injury has occurred or is likely to occur. Various operations of devices described above can also serve as elements of methods in various embodiments herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A monitoring system to detect acute kidney injury comprising:
   a first implantable device comprising one or more sensors configured to measure renal data;
   a sensor circuit configured to collect the renal data from the one or more sensors, the renal data comprising at least one of hydration status, creatinine levels, and urine volume;
   a memory circuit to store the collected renal data and renal-relevant extracorporeal data;
   an evaluation circuit configured to receive the collected renal data from at least one of the sensor circuit and the memory circuit; and
   a telemetry circuit in electronic communication with at least one of the sensor circuit and the evaluation circuit;
   wherein the evaluation circuit is configured to assess renal status and determine whether acute kidney injury has occurred by comparing the collected renal data to at least one of threshold values, personal historical values, patient population values, and patterns indicative of acute kidney injury;

wherein the evaluation circuit is configured to initiate a warning notification if acute kidney injury has occurred; and wherein the evaluation circuit is configured to classify the acute kidney injury into pre-renal, intrinsic renal, and post renal.

2. The monitoring system of claim 1, further comprising a remotely located server, wherein the telemetry circuit conveys the renal data to the remotely located server containing the evaluation circuit, the remotely located server configured to execute a pattern recognition algorithm to assess renal status and determine whether acute kidney injury has occurred.

3. The monitoring system of claim 1, wherein the evaluation circuit estimates at least one of glomerular filtration rate and fractional excretion of filtered sodium.

4. The monitoring system of claim 1, the renal data further including at least one of volumetric status, or hemodynamic status.

5. The monitoring system of claim 1, wherein the evaluation circuit evaluates historical data regarding the patient related to acute kidney injury, the historical data including historical renal data and past incidents of acute kidney injury.

6. The monitoring system of claim 1, wherein the data used by the evaluation circuit includes pharmaceutical usage data.

7. The monitoring system of claim 1, wherein the evaluation circuit is further configured to receive and evaluate medical procedural data.

8. The monitoring system of claim 1, wherein the evaluation circuit assigns an index of severity after determining whether acute kidney injury has occurred.

9. The monitoring system of claim 1, the evaluation circuit configured to generate a recommended therapeutic response after determining that acute kidney injury has occurred.

10. The monitoring system of claim 9, wherein the recommended therapeutic response is dependent on whether the acute kidney injury is caused by pre-renal or intrinsic renal factors.

11. The monitoring system of claim 9, wherein the recommended therapeutic response is accompanied by information indicating whether the acute kidney injury is caused by pre-renal or intrinsic renal factors.

12. The monitoring system of claim 1, further comprising a device configured to deliver device based therapies comprising baroreceptor modulation, spinal cord stimulation, and/or renal denervation/stimulation, wherein the device is configured to receive instructions from the system.

13. The monitoring system of claim 1, further comprising a second implantable device or a wearable device.

14. The monitoring system of claim 1, wherein the system is configured to send instructions to a patient to seek immediate medical therapy or to a device that can deliver device based therapies.

15. The monitoring system of claim 1, wherein the evaluation circuit is configured to generate a recommended therapeutic response after classifying the acute kidney injury.

\* \* \* \* \*